United States Patent [19]

Mühlemann et al.

[11] Patent Number: 5,124,143
[45] Date of Patent: * Jun. 23, 1992

[54] DENTRIFICE

[75] Inventors: Hans R. Mühlemann, Zürich, Switzerland; Karl-Hans Müller, Bruchköbel; Matthias Neumüller, Hasselroth, both of Fed. Rep. of Germany

[73] Assignee: Degussa AG, Fed. Rep. of Germany

[*] Notice: The portion of the term of this patent subsequent to May 5, 2009 has been disclaimed.

[21] Appl. No.: 281,948

[22] Filed: Dec. 7, 1988

Related U.S. Application Data

[63] Continuation of Ser. No. 123,317, Nov. 20, 1987, abandoned.

[30] Foreign Application Priority Data

Nov. 21, 1986 [DE] Fed. Rep. of Germany ....... 3639844

[51] Int. Cl.⁵ .................. A61K 7/16; C01B 33/12; C09K 3/14
[52] U.S. Cl. ...................... 424/49; 51/308; 51/311; 423/335; 423/339; 424/52; 106/DIG. 2
[58] Field of Search ............ 423/335, 339; 424/49, 424/52; 106/DIG. 2; 51/308, 311

[56] References Cited

U.S. PATENT DOCUMENTS

| 3,864,470 | 2/1975  | Watson        | 424/49  |
|-----------|---------|---------------|---------|
| 3,928,541 | 12/1975 | Wason         | 423/339 |
| 4,122,161 | 10/1978 | Wason         | 424/49  |
| 4,340,584 | 7/1982  | Wason         | 424/54  |
| 4,356,107 | 10/1982 | Payne         | 51/308  |
| 4,420,312 | 12/1983 | Wason         | 51/308  |
| 4,421,527 | 12/1983 | Wason         | 51/308  |
| 4,495,167 | 1/1985  | Nauroth et al.| 423/339 |

FOREIGN PATENT DOCUMENTS 1293138 4/1969 Fed. Rep. of Germany.
3114493 10/1982 Fed. Rep. of Germany.

OTHER PUBLICATIONS

Stockhausen Bulletin on "Skin Cleaning".
Perlite Technical Data Sheet/No. 2-1 1980.
"Basic Facts About Perlite" pub. by Perlite Institute Inc N.Y. publication No. BF-76.

Primary Examiner—A. Lionel Clingman
Assistant Examiner—Linda D. Skaling
Attorney, Agent, or Firm—Cushman, Darby & Cushman

[57] ABSTRACT

The toothpaste for preventative oral hygiene contains a mixture of synthetically prepared precipitated silicic acid and perlite in addition to a solvent as cleaning body.

A mixture consisting of glycerol (86%) and water is used as solvent.

6 Claims, 4 Drawing Sheets

Fig. 1

Fig. 3 COMMERCIALLY AVAILABLE PROPHYLACTIC PASTE

DENTRIFICE

This is a continuation of application Ser. No. 07/123,317 filed Nov. 20, 1987, which was abandoned upon the filing hereof.

BACKGROUND OF THE INVENTION

Dentifrices used for oral hygiene generally includes three different types of paste, classified according to hardness (hard, medium and soft). The structure of these pastes is not comparable to a conventional toothpaste. Rather, it is similar to a polishing paste whose consistency is nearly crumbly. This crumbly structure is necessary when the dentifice is used in the buccal cavity with a polishing device in order to avoid loss of substance by e.g. spraying. These pastes are used by dental hygienists as a supplement to daily dental care in order to remove stubbornly adhering dental plaque. This additional treatment is intended to support oral hygiene in such a manner that caries are reduced, thus rendering dental treatment almost superfluous. Experience has shown that a cleaning every two months is necessary for a good effect. The minimum frequency for this type of care is twice a year.

When carrying out the additional care, the dental hygienist first treats the plaque with the hard paste, then with the medium-hard paste and finally with the soft paste. A roughening of the tooth surface is sought with the hard paste, in order to embed the fluorocomponents of the dentifrice so as to obtain a long-lasting action in this rough surface. The medium-hard and the soft pastes are intended to polish away the coarsest unevenness on the tooth.

Known dentifrices for preventative dental hygiene prophylaxis also contain pumice, zircon silicate or hard $Al_2O_3$ in addition to silicates. This makes it possible to achieve RDA values of 250 (hard paste), 120 (medium-hard paste) and 40 (soft paste). Tests have shown that the copper abrasion of these three variants is relatively high at 70-100 mg Cu, but not very different.

SUMMARY OF THE INVENTION

The object of the invention is to provide a dentifrice for preventative oral hygiene which contains, as polishing body, a mixture consisting of a synthetically produced precipitated silicic acid and perlite.

The dentifrice of the invention can contain, in addition to the polishing body, which can constitute 30-50% by weight of the total dentifrice, 50-70% by weight of a solvent mixture consisting of glycerol (86%) and water. The solvent mixture can consist of glycerol (86%) and water in any ratio, preferably 1:1.

The amount of synthetically produced precipitated silicic acid can exceed the amount of perlite in the polishing body. This brings about an average abrasiveness. The polishing body can contain primarily amorphous precipitated silicic acid in order to reduce the abrasiveness. The ratio of perlite to precipitated silicic acid can be 1:1 to 1:6, depending on the abrasiveness desired.

In one embodiment of the invention, the dentifrice can contain a precipitated silicic acid obtained by homogeneously mixing silicic acids of different particle size and particle density, obtained in a customary manner by precipitation, with each other in the suspension phase and processing the mixtures in a customary manner by filtering, washing, drying and grinding.

In a preferred embodiment of the invention, the dentifrice can contain a precipitated silicic acid with the following physical and chemical characteristic data:

| | | |
|---|---|---|
| Drying loss (DIN 53 198) | % | 3-7 |
| Conductivity at 25° C. (4% suspension) | μS | 400-800 |
| pH (5% according to DIN 53 200) | | 6-7 |
| BET surface (DIN 66 131) | m²/g | 130-150 |
| Tamped density (DIN 53 194) | g/l | 100-150 |
| Macropore volume D > 30 nm (according to the Hg injection method) | ml/g | 3.2-4.0 |
| Oil absorption acc. to Gardner | ml/100 g | 180-200 |
| Water retention capacity | % | 76-79 |
| Cu abrasion | mg | 5-14 |
| RDA abrasion | | 35-100 |
| REA abrasion | | 40-90 |
| Scratches | | few-very few |
| Viscosity (in 16% glycerol-water dispersion 1:1 spindle D with helipath) | mPas | 5000-10,000 |
| Fe content | ppm | 240-280 |

In particular, the dentifrice of the invention can contain a precipitated silicic acid with the following physical and chemical data

| | | |
|---|---|---|
| Drying loss (DIN 53 198) | % | 3-7 |
| Conductivity at 25° C. (4% suspension) | μS | 400-800 |
| pH (5% according to DIN 53 200) | | 6-7 |
| BET surface (DIN 66 131) | m²/g | 130-150 |
| Tamped density (DIN 53 194) | g/l | 100-150 |
| Macropore volume D > 30 nm (according to the Hg injection method) | ml/g | 3.2-4.0 |
| Oil absorption acc. to Gardner | ml/100 g | 180-200 |
| Water retention capacity | % | 76-79 |
| Cu abrasion | mg | 5-14 |
| RDA abrasion | | 35-100 |
| REA abrasion | | 40-90 |
| Scratches | | few-very few |
| Viscosity (in 16% glycerol-water dispersion 1:1 spindle D with helipath) | mPas | 5000-10,000 |
| Fe content | ppm | 240-280 | which is prepared as follows:

A thickening precipitated silicic acid suspension is prepared by reacting alkali silicate solutions with an acid while avoiding the formation of a gel. To this end, the acid is fed into a vessel which contains an alkali silicate solution which has a concentration of approximately 5 g to 25 g $SiO_2$ liter solution, at certain solution concentrations and certain feed speeds, while maintaining a precipitation temperature in the reaction medium between 80 and 90° C. The viscosity of the reaction medium is held steadily low for a period of at least 30% of the total precipitation time, the pH is held between 10 and 12 and the addition of the reactants is ended before the viscosity has dropped, after having passed through a maximum, to a value less than 100% over the initial viscosity. Then the acidity is adjusted with sulfuric acid to a pH less than 7.

In addition, an abrasive precipitated silicic acid suspension is prepared as follows: An original precipitated silicic acid suspension is prepared by precipitating silicic acid from an alkali silicate solution in a vessel with a concentration of approximately 5 - 25 g SiO2 per liter solution with an acid and alkali metal silicate solution with certain solution concentrations and certain feed speeds while maintaining a precipitation temperature in the reaction medium between 80 and 90° C The mixture is intensively sheared, if necessary, during the entire precipitation time. The viscosity of the reaction medium is held steadily low for a time period of at least 30% of the total precipitation time and the pH is held between 10 and 12, and the addition of the reactants is ended before the viscosity has dropped, after having passed through a maximum, to a value less than 100% over the initial viscosity. Then the pH is set with sulfuric acid to 7-9, the mixture is thinned with hot water to a precipitated silicic acid content of 10-30 g/l and a sodium sulfate content of 6-29 g $Na_2SO_4$/l, heated to 80-90° C. Next a precipitated silicic acid final concentration of 40 to 80 g/l is set while maintaining this pH constant by simultaneously feeding in alkali metal silicate solution, sulfuric acid and, optionally, hot water for a precipitation time of 15 to 180 minutes and the suspension is acidified with sulfuric acid to a pH under 7.

Then the respective precipitated silicic acid suspensions are mixed with one another, the precipitated silicic acid is filtered off, washed, spray-dried and subsequently the product is ground in a compressed-air mill.

In preferred embodiment of the invention the thickening silicic acid suspension is prepared essentially according to German Patent Specification DE-AS 14 67 019, the disclosure of which is incorporated herein by reference.

The abrasive precipitated silicic acid suspension is preferably prepared essentially according to DE-OS 31 14 293 the disclosure of which is incorporated by reference, especially Example 10.

It was found that especially valuable precipitated silicic acids for usage in dentifrices can be obtained by mixing precipitated silicic acids of different properties in the suspension phase. Precipitated silicic acid suspensions which are suitable for this purpose can be obtained directly by precipitation or by resuspending precipitated silicic acid filter press paste. Precipitated silicic acid suspensions prepared directly by precipitation are preferred.

The precipitated silicic acids made by mixing of precipitated silicic acid suspensions, filtering, drying and grinding in accordance with the invention exhibit more advantageous properties in dentifrices than a mixture made by dry blending of the same initial precipitated silicic acid in the same proportions.

Figure 1:
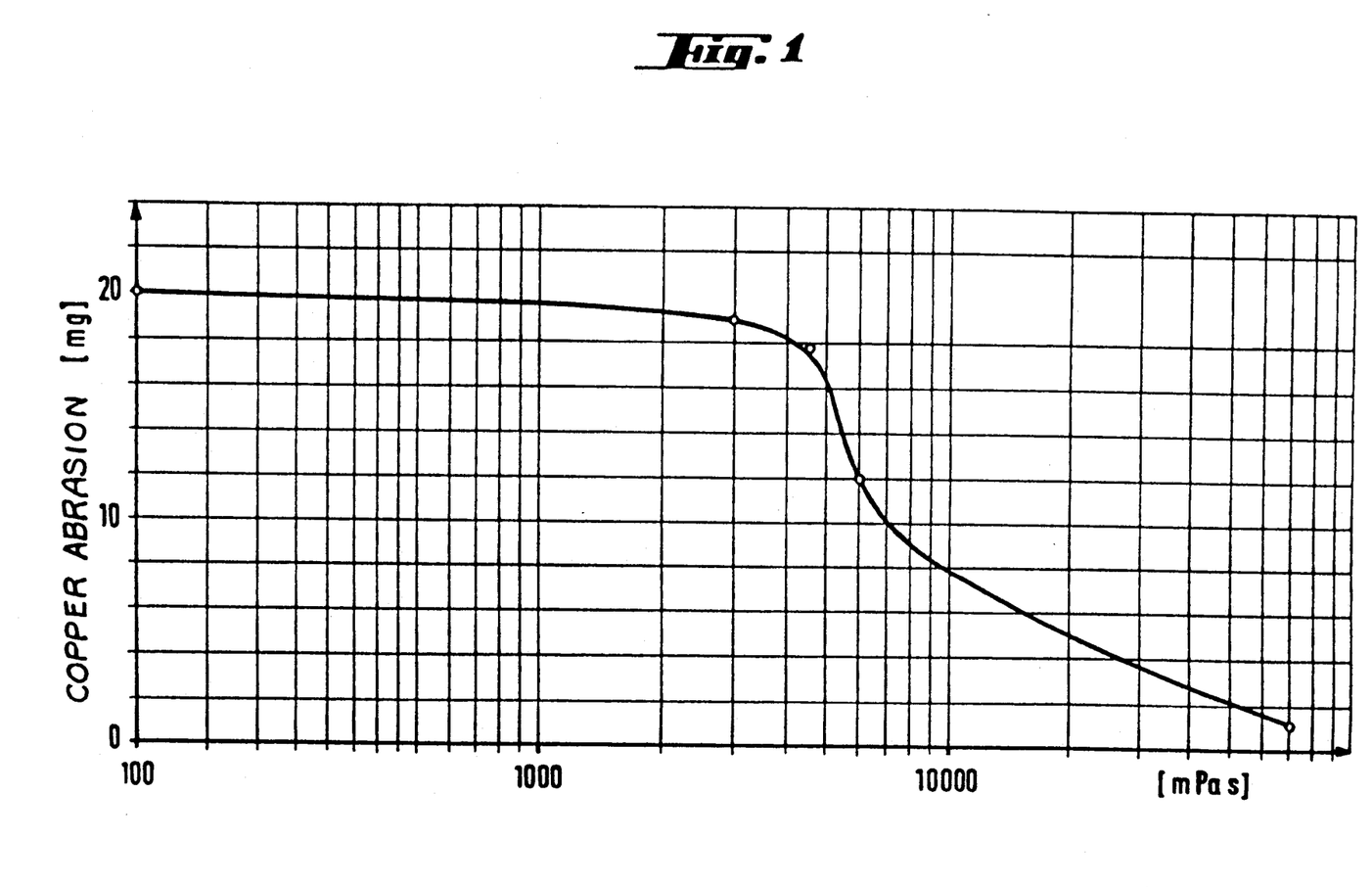
FIG. 1 is a graph which shows the viscosity-abrasiveness relationship of precipitated silicic acids made by mixing a suspension of precipitated silicic acids in accordance with the invention.

The precipitated silicic acids made by mixing suspensions of precipitated silicic acids, in accordance with the invention, exhibit synergistic effects in such a manner that at a given viscosity or thickening action, an unexpectedly high abrasiveness occurs, that is, the viscosity-abrasiveness relationship is surprisingly not linear (cf. FIG. 1). These precipitated silicic acids are particularly easy to prepare because the amounts can be exactly adjusted continuously or in batches by means of suitable volumetric or weight measurements at known solid contents. In addition, the wet process advantageously poses no dust problems. Also, separation phenomena are minimized.

Apparently, the components in mixtures made by mixing suspensions of precipitated silicic acids lose a part of their identity, in contrast to dry mixtures. During mixing, and probably especially during drying, reciprocal actions of small particles with larger particles occur, whereby the small particles settle or are washed onto larger particles. Even different forms of mutual flocculation and penetration in the aqueous phase may be considered.

Figure 2:
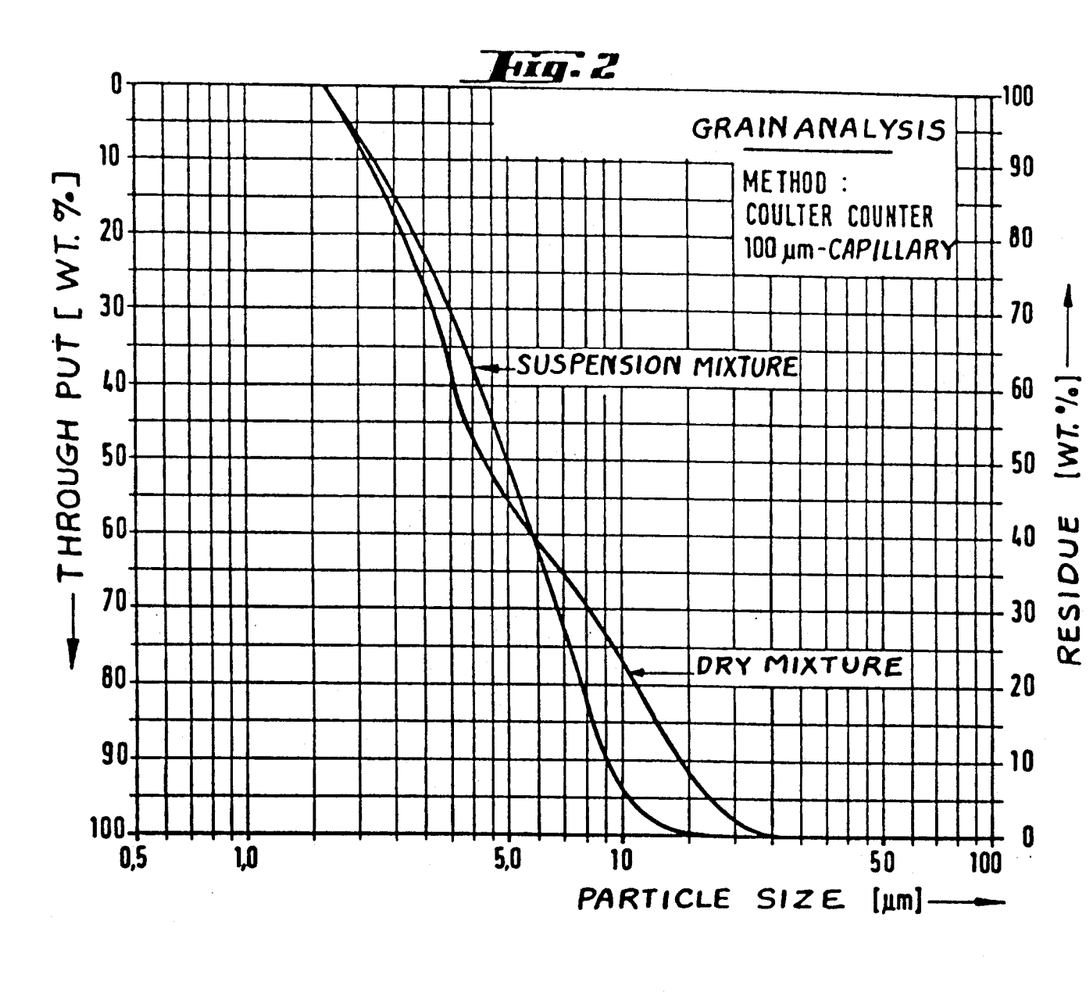
FIG. 2 shows the measurement in a Coulter counter of silicic acid mixtures made by dry mixing and wet mixing.

A first distinct difference between dry mixing and wet mixing results from the particle size distribution of the ground specimens. While the dry mixing of two precipitated silicic acids with different grain size and density during measurement in a Coulter counter showed 2 maxima as expected and the corresponding curve had a hump, the curve of the same precipitated silicic acids, mixed wet with each other in the same proportion, is completely harmonic (of FIG. 2).

Another noticeable difference consists in the thickening action. The precipitated silicic acid of the invention raises the viscosity of a mixture of glycerol and water distinctly less than the dry mixture does.

Precipitated silicic acids with moderate thickening power permit higher degrees of filling and therewith the preparation of pastes with "full" character. Low-filled pastes, on the other hand, feel "empty" or "watery" in the mouth.

The thickening action of the precipitated silicic acid must fully develop when worked into the dentifrice mass, that is, no change of the rheological behavior of the dentifrice may occur thereafter which would make it more difficult or even impossible to fill and later to empty the tubes and containers.

Basically, a dentifrice should support or increase the cleaning action of a toothbrush as a film is built up between brush and tooth surface which mechanically removes dental plaque. This action can only be achieved by means of abrasive properties.

Naturally, given the same REA abrasion, precipitated silicic acids are to be preferred which produce the fewest scratches.

The precipitated silicic acids of the invention, obtained by mixing suspensions of precipitated silicic acids of different properties, combine in an advantageous manner requirements of stable viscosity development in a medium range with high abrasive and cleaning action while avoiding deep scratches.

The measuring of abrasiveness is performed on extracted human teeth, which are rendered radioactive, on the exposed dentin (RDA value) or on the enamel (REA value). In each instance, the increase in the radioactivity of the suspension of the dentifrice to be tested is measured according to a defined treatment of the test teeth with brushes. As a substitute, the weight decrease of copper plates can be determined when brushing with a test suspension. However, the values obtained in this manner frequently are not be comparable with RDA and REA values.

Information is obtained in special laboratories about the cleaning and polishing action of dentifrices with refined, e.g. microscopic methods, whereby specimens which cause many or deep scratches are eliminated. These tests are performed on extracted animal or human teeth.

DETAILED DESCRIPTION OF PREFERRED EMBODIMENTS

In the examples which follow, the solid content (precipitated silicic acid content) of the precipitated silicic acid suspension is determined as follows:

250 ml of the precipitated silicic acid suspension cooled to 20° C are filtered by suction on a porcelain filter (0 120 mm) and thereafter the filter cake is washed with 500 ml deionized water. The cake is dried at 105° C until the weight is constant. Calculation: g weighed analytical product $\times 4$ = g solid/l

Example 1

A precipitated silicic acid with thickening action is prepared essentially according to the disclosure of German Patent Specification DE-AS 14 67 019. However, in contrast to the disclosure of this specification, concentrated sodium silicate solution (density = 1.353 g/ml) and concentrated sulfuric acid (96%) are used for reasons of economy. This results in a solid content of 85 g/l in the precipitated silicic acid suspension.

73 liters of hot water and 5.25 liters of sodium silicate solution (density = 1.353 g/ml, modulus $SiO_2$:$Na_2O$ = 3.46) are heated with agitation to 85° C in a rubber-lined 120 liter precipitation vessel. 16.5 liters of sodium silicate 1.353 g/ml, modulus SiO2:Na2O = solution (density = 1.353 g/l, modulus $SiO_2$: $Na_2O$ = 3.46) and 1.448 liters of sulfuric acid (96%) are fed simultaneously, at 11.0 liters per hour and at 0.965 liters per hour respectively, into this prepared alkaline precipitated mixture during the following 90 minutes, while the mixture is agitated and the temperature is maintained at 85° C. The addition of the reactants is ended before the viscosity of the reaction medium has dropped, after having passed a maximum, to a value less than 100% over the initial viscosity.

Thereafter, the precipitated silicic acid suspension obtained in this manner is adjusted to a pH of 3.5, by introducing sulfuric acid (96%) for several minutes at 1.25 liters per hour. The precipitated silicic acid suspension obtained in this manner has a solid content of 85.0 g/l.

The precipitated silicic acid obtained after the filtering, washing, spray-drying and grinding in a compressed-air mill has the physical and chemical characteristics listed in Table 1.

Example 2

This example describes the preparation of an abrasive precipitated silicic acid according to the disclosure of German Patent Specification DE-OS 31 14 493, Example 10. However, the entire amount of water is added to the precipitated flask, which eliminates the addition of water during the precipitation and the precipitation time is extended from 60 to 100 minutes.

73 liters of hot water and 5.25 liters of sodium silicate solution (density = 1.353 g/ml; modulus: $SiO_2$:$Na_2O$ = 3.46) are heated under agitation to 85° C in a rubber lined 120 liter precipitation vessel. 16.5 liters of sodium silicate solution (density = 1.353 g/ml; modulus $SiO_2$ $Na_2O$ = 3.46) and 1.448 liters concentrated sulfuric acid (96%) are added simultaneously at 11.0 liters per hour and 0.965 liters per hour respectively into this prepared alkaline precipitated mixture during the following 90 minutes with agitation and the temperature is maintained at 85° C. The addition of the reactants is ended before the viscosity of the reaction medium has dropped, after having passed a maximum, to a value less than 100% over the initial viscosity.

Thereafter, the pH of the precipitated silicic acid suspension obtained in this manner is adjusted to 8.5, by adding concentrated sulfuric acid (96%) for several minutes at 1.25 liters per hour. The precipitated silicic acid suspension obtained in this manner has a solid content of 85 g/l. Its $Na_2SO_4$ content is 55 g/l.

Intensive shearing is performed during the entire precipitation time of 90 minutes by means of a centrifugal pump which rotates the container contents several times. More precise details about the apparatus and the shearing conditions are found in German Patent Specification DE-PS 17 67 332, the disclosure of which is incorporated herein by reference, and in particular in column 8, lines 31-68 of this document.

The original precipitated silicic acid suspension prepared in this manner is adjusted with water to a precipitated silicic acid content of 13 g/l and 8.5 g $Na_2SO_4$/l. 16.06 liters of this suspension are heated in a rubber lined 120 liter precipitation vessel with agitation to 85° C. 23.1 liters sodium silicate solution (density = 1.353 g/ml; modulus $SiO_2$:$Na_2O$ = 3.46) was added and 1.94 liters of sulfuric acid (96%) were added simultaneously at rates of 231.0 ml/min and 19.4 ml/min respectively to the precipitated silicic acid suspension while maintaining this temperature and a pH of 8.5 for 100 minutes. The pH of the precipitated silicic acid suspension is subsequently adjusted with sulfuric acid (96%) to approximately 3.5. The precipitated silicic acid suspension obtained has a solid content of 92.0 g/l.

The precipitated silicic acid obtained after filtering off and washing out has the physical and chemical characteristic data listed in Table 1.

EXAMPLE 3

18.05 m³ suspension of the abrasive precipitated silicic acid suspension with a precipitated silicic acid content of 92.0 g/l according to Example 2 are mixed with 40.0 m³ suspension of a thickening precipitated silicic acid according to Example 1 with a precipitated silicic acid content of 85.0 g/l in a weight ratio of 1:2-(in relation to the precipitated silicic acid content).

For further processing, the precipitated silicic acid of this suspension mixture is separated off by filter pressing. The precipitated silicic acid content in the filter press paste is 24%. The filter press paste is washed and spray-dried and the product is ground with compressed air. The precipitated silicic acid obtained exhibits the physical and chemical characteristic data listed in Table 1.

TABLE 1

|  |  | Ex. 1 | Ex. 2 | Ex. 3 |
| --- | --- | --- | --- | --- |
| Drying loss (DIN 53 198) | % | 5 | 5 | 5 |
| Conductivity at 25° C. (4% suspension) | uS | 730 | 460 | 740 |
| pH (5% according to DIN 53 200) |  | 6.3 | 6.9 | 6.3 |
| BET surface (DIN 66 131) | m²/g | 185 | 40 | 140 |
| Tamped density (DIN 53 194) | g/l | 80 | 240 | 130 |
| Macropore volume D > 30 nm (according to the Hg injection method) | ml/g | 3.8 | 1.1 | 3.0 |
| Oil absorption | ml/100 g | 280 | 80 | 184 |

TABLE 1-continued

|  |  | Ex. 1 | Ex. 2 | Ex. 3 |
|---|---|---|---|---|
| acc. to Gardner |  |  |  |  |
| Water retention capacity | % | 80 | 56 | 76 |
| Cu abrasion | mg | 1 | 20 | 12 |
| RDA abrasion |  | 23 | 170 | 80 |
| REA abrasion |  | 25 | 130 | 70 |
| Scratches |  | very few | many | few |
| Viscosity (in 15% water-dispersion 1:1 Spindle D with helipath) | mPas | 72,000 | <100 | 6,000 |
| Fe content | ppm | 260 | 240 | 240 |

The physical and chemical characterizing data are determined as follows:

Drying loss according to DIN 53 198.
Conductivity at 25° C.
4% suspension

A specimen of 4.0 g is heated with 50 ml of completely desalinated water in a 150 ml beaker glass and boiled for one minute with agitation. Subsequently, the suspension is transferred into a 100 ml flask, cooled down and filled up to the mark with completely desalinated water. The electric conductivity is measured with a commercially available measuring device, e.g., of the "Wissenschaftlich-Technischen Werkstatten" [Scientific-Technical Workshops](WTW) conductometer type LF 530 at 25° C. pH in 5% aqueous dispersion according to DIN 53 200.

BET surface according to DIN 66 131.

A specimen is rinsed with nitrogen at 100° C. The volumetric measurement is performed with superpure nitrogen at the temperature of liquid nitrogen ($-195.8°$ C.).

Tamping density according to DIN 53 194.

The test is performed without pretreatment of the specimen.

Macropore volume D>30 nm according to the Hg pressure method.

The measurement is performed with the Mercury Pressure Porosimeter, 200 Series, from the firm Carlo Erba Strumentazione.

Oil absorption acc. to Gardner-Coleman

According to ASTM : D 1483-60,

Water retention capacity

The water retention capacity indicates the water amount contained, after pressing the precipitated silicic acid suspension and washing out until electrolytically poor, in a paste press. 250 g press paste is dried to weight constancy at 105° C. for measurement. Calculation:

$$100 - \frac{\text{weighed analytical product} \times 100}{\text{weight of sample}} = \% \text{ water retention capacity}$$

Particle size distribution

According to the Coulter/100 m cap.

The measurement is performed with a Coulter counter model TA II of the firm Coulter Electronics GmbH DETERMINATION OF THE CU ABRASION IN 10% GLYCEROL DISPERSION a) Preparation of the glycerol dispersion 153 g glycerol (water-free, superpure Ph Eur, BP USP, density =1.26 g/ml, from the firm Merck, Darmstadt) are weighed in a polyethylene beaker (250 ml). 17 g precipitated silicic acid are carefully mixed in with a spatula. The mixture is subsequently homogenized with a blade agitator (diameter 5.2 cm) for 12 minutes at 1,500 rpms.

b) Performance of the abrasion measurement

The determination of the abrasion measurement is performed in an abrasion testing device which is known from the following publications: (1) Pfrengle: "Fette, Seifen, Anstrichmittel" [Fats, Soaps, Paints]63 (5), 1961, pages 445 to 451 "Abrasion and Cleaning Power of Polishing Bodies in Toothpastes"; (2) A. Reng, F. Dany: "Parfumerie und Kosmetik" [Perfume and Cosmetics]59 (2), 1978, pages 37 to 45 "Technical Testing of the Use of Toothpastes". To this end, the 6 troughs of the test device are each coated with 20 ml of the homogeneous dispersion. The abrasion, brought about by six smoothly ground nylon brushes on six smoothly ground Cu sheets (electrolyte - copper) in five hours with 50,000 double strokes, is determined by differential weighing. Average values are determined from the obtained values in the calculation of the abrasiveness. The abrasion (abrasiveness) is indicated in mg Cu.

RDA ABRASION

REA-ABRASION

The RDA method is described in the Journal of Dental Research, 55 (4), 563, 1976 and is also used for the REA abrasion Scratches are visually determined with a microscope.

Determination of the viscosity

Measured in a 16% glycerol/water dispersion (mixture 1:1) with a Brookfield viscosity meter RTV, spindle 10, with helipath at 10 rpms.

| 1. Test batches |
|---|
| 48 g silicic acid |
| 126 g glycerol (approximately 87%, superpure Ph Eur. BP, density = 1.23 g/ml from the firm Merck, Darmstadt) |
| 126 g distilled water |
| 300 g 16% dispersion in relation to silicic acid |

2. Performance

The abrasive silicic acids were stirred by hand in a 400 ml beaker glass (wide form) into the glycerol/water mixture with a glass rod and allowed to stand 24 hours. Then, the viscosity is measured.

3. Measurement

The viscosity measurement is performed in the same beaker glass with a Brookfield viscosity meter RVT, spindle 10, with helipath at 10 rpms.

4. Calculation

Read-off scale value x factor =viscosity in mPas.

Pastes for prophylaxis (according to the invention)

1. Mixing together of the powdery components in a turbulamixer (5 min.).
2. Preparation of the solvent mixture glycerol (86%) and distilled water at a ration of 1:1.
3. Preparation of the pastes The powdery components are put in a 600 ml beaker glass, tared on a balance and the solvent mixture is stirred in with a spatula portions until a consistency similar to that of Nupro pastes has been reached, then 1% aromatic oil is added (peppermint). The mixture was then passed again through a 1 mm sieve for homogenization. The composition of the paste is then calculated from the weight of the carrier and the added amount of solvent.

The precipitated silicic acid of Example 3 is used as precipitated silic acid.

Perlite 2000 is a perlite with the following physical and chemical characteristic data:

| | |
|---|---|
| Color | white |
| Bulk density | 80.0 g/l |
| Water content | 0.5% |
| Ignition loss | 1.0% |
| pH | 8.5 |
| Wet density | 150.0 g/l |
| Transit value | 450.0 ml |
| Coarse particles, not precoatable | 1.0% |

| Particle-size distribution/particle-size | | | | | | | | | |
|---|---|---|---|---|---|---|---|---|---|
| <2 | 2-6.3 | 6.3-10 | 10-20 | 20-45 | 45-63 | 63-90 | 90-125 | 125-200 | >200 |
| 1 | 4 | 5 | 15 | 10 | 25 | 15 | 10 | 10 | 5 |

| Chemical analysis | |
|---|---|
| $SiO_2$ | 75.0% |
| $Fe_2O_3$ | 2.0% |
| $Al_2O_3$ | 13.0% |
| CaO | 0.5% |
| $K_2O$ | 4.0% |
| MgO | Trace |
| $Na_2O$ | 5.0% |

The compositions of the prepared pastes are given in Table 2:

TABLE 2

| | Paste | | | | | | |
|---|---|---|---|---|---|---|---|
| | 1 hard paste | 2 | 3 | 4 | 5 | 6 soft paste | 7 |
| Perlite | 22.00 | 13.00 | 9.50 | 7.20 | 6.00 | 5.00 | — |
| precipitated silicic acid | 22.00 | 26.00 | 28.50 | 28.80 | 30.00 | 30.00 | 35.00 |
| Desalinated Water | 22.00 | 27.00 | 28.00 | 30.00 | 30.00 | 31.00 | 31.00 |
| Glycerol | 33.00 | 33.00 | 33.00 | 33.00 | 33.00 | 33.00 | 33.00 |
| Aromatic oil | 1.00 | 1.00 | 1.00 | 1.00 | 1.00 | 1.00 | 1.00 |
| | 100.00 | 100.00 | 100.00 | 100.00 | 100.00 | 100.00 | 100.00 |

Ratio of perlite 2000 to precipitated silicic acid in the pastes:

Paste 1 Perlite 2000:precipitated silicic acid = 1:1
Paste 2 Perlite 2000:precipitated silicic acid = 1:2
Paste 3 Perlite 2000:precipitated silicic acid = 1:3
Paste 4 Perlite 2000:precipitated silicic acid = 1:4
Paste 5 Perlite 2000:precipitated silicic acid = 1:5
Paste 6 Perlite 2000:precipitated silicic acid = 1:6
Paste 7 Perlite 2000:precipitated silicic acid = 0:1

Pastes 1 and 2, which exhibit a ratio of perlite to precipitated silic acid of 1:1 to 1:2, are hard pastes.

Pastes 3 and 4, which exhibit a ratio of perlite to precipitated silic acid of 1:3 to 1:4, are medium-hard pastes.

Pastes 5 and 6, which exhibit a ratio of perlite to precipitated silicic acid of 1:5 to 1:6, are soft pastes.

Paste 7, which contains no perlite, is too soft.

Pastes which do not exhibit this mixing ratio are not stable in storage.

DESCRIPTION OF THE PASTES

Perlite 2000 is the more abrasive component in comparison to precipitated silicic acid but it has almost no absorptivity or absorption capacity. Thus, there is no possibility of shifting the ratio of perlite 2000 : precipitated silicic acid 1:1 in favor of perlite 2000 since the paste would otherwise become unstable and separate liquid and the sediment would become very hard. In the opposite case, however, a paste can be prepared with precipitated silicic acid alone.

Perlite 2000 has a high abrasiveness and therefore causes grooves on the tooth surface. The use of precipitated silicic acid as polishing body of average abrasiveness can decisively improve the grooving value.

EVALUATION DIAGRAMS OF SCRATCH VALUE DETERMINATIONS OF COMMERCIAL PROPHYLAXIS PASTES (NUPRO) AND PRECIPITATED SILICIC ACID/PERLITE 2000 PASTES

The Nupro pastes exhibit a much more disadvantageous action on the tooth enamel. The grooving or scratch value of the individual pastes is evaluated as follows:

| Pastes | Scratch value after 30 min | RDA value | Cu abrasion (mg Cu) |
|---|---|---|---|
| Nupro - hard | 800 | not known | 75 |
| Nupro - medium-hard | 367 | not known | 85 |
| Nupro - soft | 212 | not known | 75 |
| precipitated silicic acid/ P 2000 hard | | 348 | 260 |
| precipitated silicic acid/ P 2000 medium hard | 122 | 266 | 380 |
| precipitated silicic acid/ P 2000 soft | 110 | 188 | 450 |

SCRATCH VALUE

Figure 3:
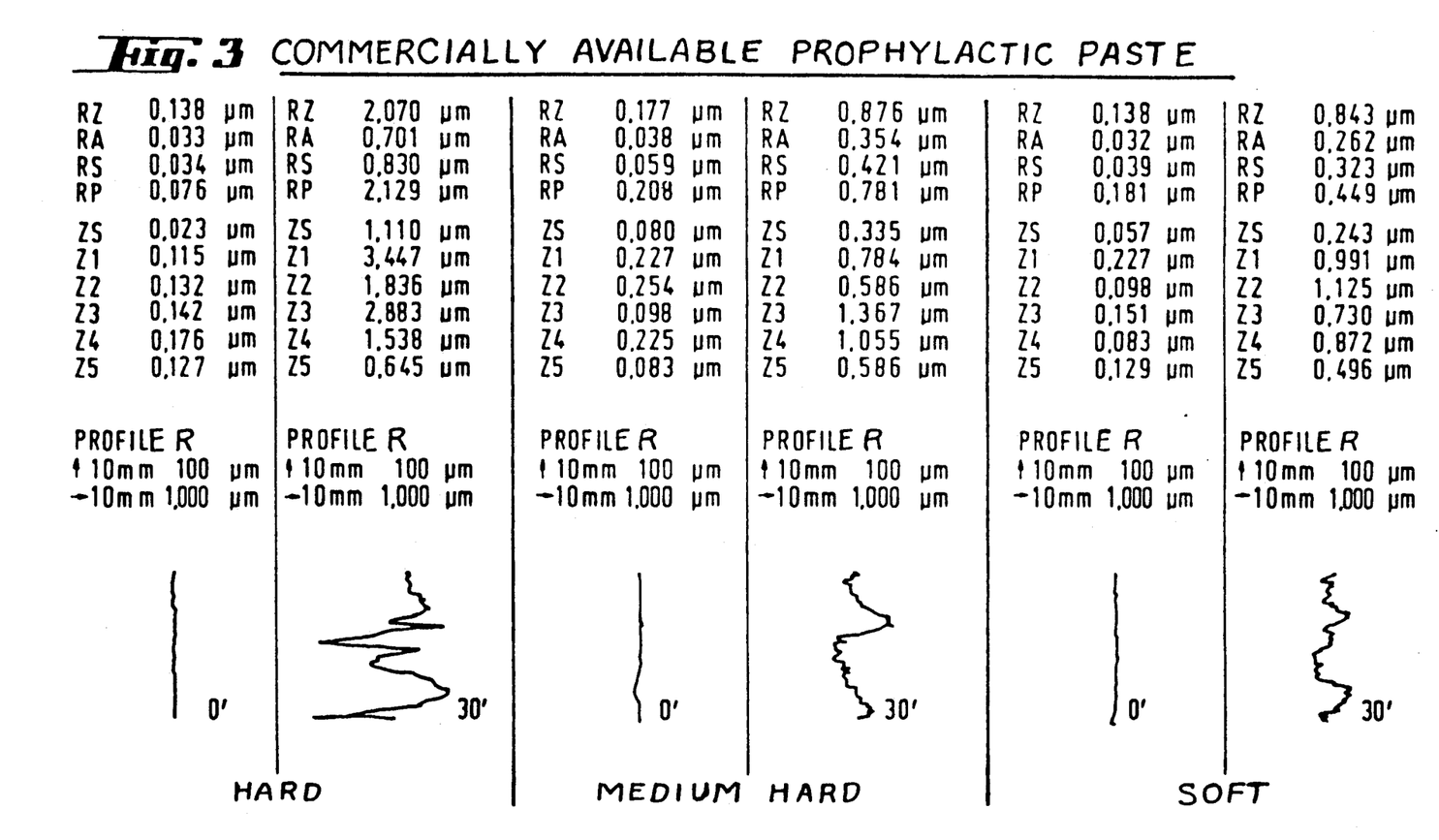
FIGS. 3 and 4 show the results of scratch value measurements for a commercially available dentrifice and the dentrifice of the invention.
Figure 4:
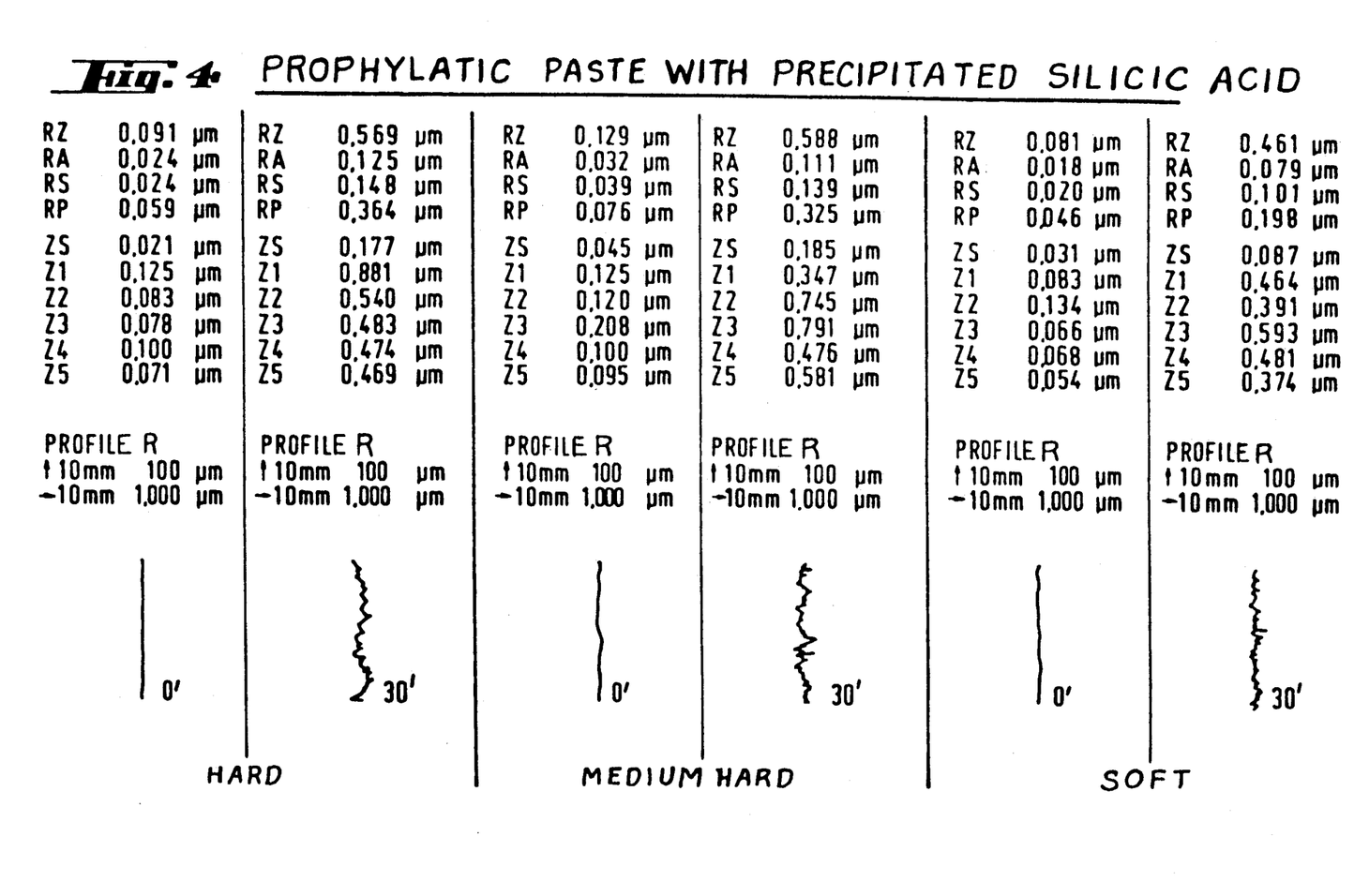

A scratch value of 100±20 is tolerated for prophylaxis pastes. By comparison, the precipitated silicic acid pastes of the invention exhibit values around 20-60. The grooving value is determined in the literature as average roughness value (RA). The measurements are performed on 4 teeth at a time, whereby a defined comparison is included in the tests. It can be seen even from the curves (FIGS. 3 and 4) that the Nupro pastes are considerably less advantageous in comparison to the pastes of the invention.

COPPER ABRASION

If the copper abrasion is considered, it remains to be determined that the cleaning power of the pastes of the invention is distinctly higher than that of the Nupro pastes and nevertheless the scratch determination shows that a more protective treatment is to be expected.

RDA VALUE

One can conclude from these results that the prophylaxis pastes of the invention have the advantage over already-known and available products in that they exhibit a distinctly higher cleaning power and yet are less harsh on the tooth enamel.

What is claimed is:

1. A dentifrice for preventative oral hygiene which contains a mixture consisting essentially of a synthetically prepared precipitated silic acid and of a perlite as polishing body, said precipitated silicic acid having the following physical and chemical properties:

| | | |
|---|---|---|
| Drying loss (DIN 53 198) | % | 3-7 |
| Conductivity at 25° C. (4% suspension) | uS | 400-800 |
| pH (5% according to DIN 53 200) | | 6-7 |
| BET surface (DIN 66 131) | m²/g | 130-150 |
| Tamped density (DIN 53 194) | g/l | 100-150 |
| Macropore volume D > 30 nm (according to the Hg injection method) | ml/g | 3.2-4.0 |
| Oil absorption acc. to Gardner | ml/100 g | 180-200 |
| Water retention capacity | % | 76-79 |
| Cu abrasion | mg | 5-14 |
| RDA abrasion | | 35-100 |
| REA abrasion | | 40-90 |
| Scratches | | few-very few |
| Viscosity (in 16% glycerol-water dispersion 1:1 spindle D with helipath) | mPas | 5000-10,000 |
| Fe content | ppm | 240-280. |

2. A dentifrice according to claim 1 which contains, in addition to 30-50% of said polishing body, 50-70% of a solvent mixture of glycerol and water.

3. A dentifrice as set forth in claim 2 in which the ratio of glycerol to water is 1:1.

4. A dentifrice according to claim 1 in which the cleaning body contains more precipitated silicic acid than perlite.

5. A dentifrice according to any one of claims 1 to 3 in which the precipitated silic acid is obtained by homogeneously mixing suspensions of precipitated silicic acids of different particle sizes and particle density with each other and preparing the mixtures by filtering, washing, drying and grinding.

6. A dentifrice according to claim 1 which contains precipitated silicic acid which has the following physical and chemical properties

| | | |
|---|---|---|
| Drying loss (DIN 53 198) | % | 3-7 |
| Conductivity at 25° C. (4% suspension) | uS | 400-800 |
| pH (5% according to DIN 53 200) | | 6-7 |
| BET surface (DIN 66 131) | m²/g | 130-150 |
| Tamped density (DIN 53 194) | g/l | 100-150 |
| Macropore volume D > 30 nm (according to the Hg injection method) | ml/g | 3.2-4.0 |
| Oil absorption acc. to Gardner | ml/100 g | 180-200 |
| Water retention capacity | % | 76-79 |
| Cu abrasion | mg | 5-14 |
| RDA abrasion | | 35-100 |
| REA abrasion | | 40-90 |
| Scratches | | few-very few |
| Viscosity (in 16% glycerol-water dispersion 1:1 spindle D with helipath) | mPas | 5000-10,000 |
| Fe content | ppm | 240-280 | said precipitated silicic acid being prepared as follows:
(a) a thickening precipitated silicic acid suspension is prepared by reacting alkali silicate solutions with an acid while avoiding the formation of a gel, for which purpose, in order to precipitate the silicic acid, the acid and an alkali silicate solution are fed into an aqueous alkali silicate solution, which has a concentration of approximately 5 g to 25 g $SiO_2$ per liter of solution, in a vessel at certain solution concentrations and certain feed speeds, while maintaining a precipitated temperature in the reaction medium between 80 and 90° C., in such a manner that the viscosity of the reaction medium is held steadily low in a period of at least 30% of the total precipitation time and the pH is held between 10 and 12 and the addition of the reaction participants is ended before the viscosity has dropped, after having passed through a maximum, to a value less than 100% over the initial viscosity and the acidity is adjusted with sulfuric acid to a pH less than 7;

(b) an abrasive precipitated silicic acid suspension is prepared by producing an original precipitated silicic acid suspension by precipitating the silicic acid from an alkali silicate solution which has a concentration of approximately 5-25 g SiO2 per liter solution, in a vessel, with an acid and alkali metal silicate solution with certain solution concentrations and certain feed speeds while maintaining a precipitation temperature in the reaction medium between 80 and 90° C., the container contents being intensively sheared, if necessary, during the entire precipitation time, the viscosity of the reaction medium being held steadily low in a time period of at least 30% of the total precipitated time and the pH being held between 10 and 12, and the addition of the reactants being ended before the viscosity has dropped, after having passed through a maximum, to a value less than 100% over the initial viscosity, then the pH is set with sulfuric acid to 7 to 9, the mixture is thinned with hot water to a precipitated silic acid content of 10-30 g/l and a sodium sulfate content of 6-29 g Na2SO4/l, and the mixture is heated to 80-90° C., and a precipitated silicic acid final concentration of 40 to 80 g/l is set while maintaining the is pH constant by simultaneously feeding in alkali metal silicate solution, sulfuric acid and, optionally, hot water for a precipitation time of 15 to 180 minutes, next the suspension is acidified with sulfuric acid to a pH under 7, (c) both precipitated silicic acid suspensions are mixed with one another and the precipitated silicic acid is filtered off, washed, spray-dried and subsequently ground in a compressed-air mill.

* * * * *